United States Patent [19]

Cohen

[11] Patent Number: 4,460,357

[45] Date of Patent: Jul. 17, 1984

[54] FLUID DISPENSING DEVICE

[76] Inventor: Milton J. Cohen, 10823 Burbank Dr., Potomac, Md. 20854

[21] Appl. No.: 392,020

[22] Filed: Jun. 25, 1982

[51] Int. Cl.³ .............................................. A61M 5/00
[52] U.S. Cl. .................................................. 604/238
[58] Field of Search ................ 604/236, 238, 218, 187

[56] References Cited

U.S. PATENT DOCUMENTS 2,893,390 7/1959 Lockhart ............................. 604/238

Primary Examiner—John D. Yasko
Attorney, Agent, or Firm—McDougall, Hersh & Scott

[57] ABSTRACT

A device in the form of a syringe having a barrel with a cylindrical neck portion in the end thereof and a plunger axially displaceable therein, a hollow needle and a hub securing the hollow needle to the open end of the barrel with a chamber in between dimensioned to have a cross section greater than the cross section of the bore and a sealing disc within the neck of the barrel mounted for displacement between sealing position for separating the needle from the barrel and unsealing position enabling fluid to flow from the barrel through the chamber to the needle.

7 Claims, 7 Drawing Figures

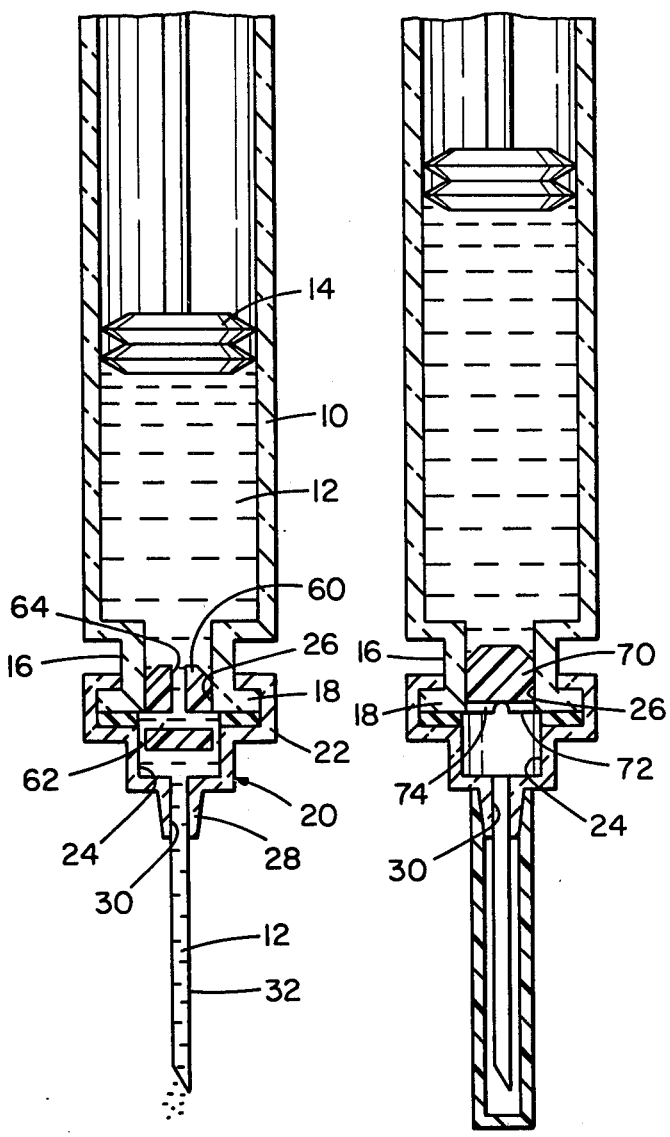
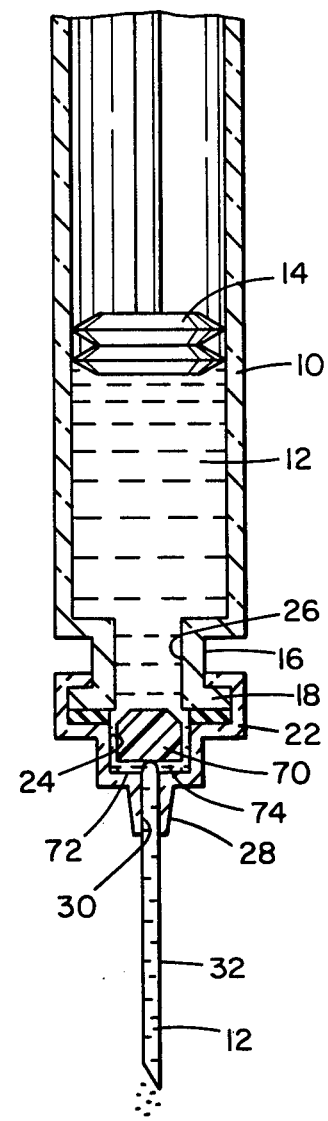
FIG.4  FIG.5  FIG.6
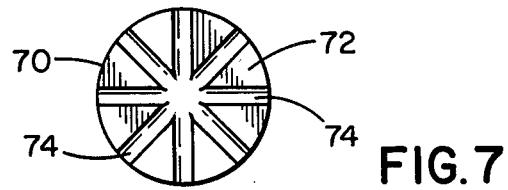
FIG.7

FLUID DISPENSING DEVICE

This invention relates to a syringe for injection of a fluid or liquid, medicaments, or the like.

BACKGROUND OF THE INVENTION

In my U.S. Pat. Nos. 3,401,693; 3,682,174; 3,757,779; 3,413,974 and 4,009,716, description is made of disposable hypodermic syringes having a barrel, the open end of which is sealed by a sealing disc member. A hollow needle is mounted within a removable cover, which aspectically houses the needle while protecting the needle against damage during periods of non-use. Means are provided for mounting the needle within the cover for piercing the sealing disc in order to gain access to the interior of the barrel to beyond the portion of the needle projecting through the sealing disc into communication with the liquid content material in the barrel. Thus the fluid or liquid content material may be dispensed from the barrel, through the needle in response to pressure applied by the various means described in the aforementioned patents.

In my previously issued U.S. Pat. Nos. 3,557,787; 3,678,931; 3,682,174; 3,757,779; 3,779,371; 3,785,397; 3,838,689; 4,055,177, and 4,234,083, description is made of a hypodermic syringe in which materials in measured amounts are contained in separate compartments with means for combining the materials in a single compartment immediately prior to use for injection of the formed solution or dispersion that is formed without exposure to elements which might otherwise bring about contamination. As in the devices previously described, the open end of the last compartment, in the form of a barrel, is sealed by a sealing disc member adapted to be pierced by a hollow needle whereby the formed solution or dispersion can be dispensed through the needle for injection and the like.

In the devices of the types described, use is made of a hollow needle, which is mounted in a hub assembly wherein the inner end of the needle is spaced a short distance from the sealing disc in order to pierce the sealing disc in response to rearward displacement of the hollow needle. Such displacement to pierce the sealing disc can be effected manually by axial displacement of the hub in which the needle is mounted, or automatically in response to the release of the needle held under tension within the hub, as by means of a spring.

In general, as described in U.S. Pat. No. 4,009,716, use is made of a ferrule and a needle hub assembly having a threaded portion at one end which threadably engages an internally threaded portion of the needle cover. The arrangement is such that, during assembly, the needle is urged to an advanced position against action of the spring or other resilient means carried by the ferrule. This enables the threaded portion of the hub to be engaged by the internally threaded portion of the cover when the latter is secured in place. The cover thus engages the ferrule to maintain the latter in the advanced position until the cover is unscrewed. This frees the ferrule to enable the spring to snap towards its relaxed position whereby the needle is projected rearwardly to bar the sealing disc member to penetrate into the barrel for communication with the interior and the material contained therein.

One of the problems in the use of assemblies of the type described, when used as a syringe, vial, or infusion bottle, resides in the tendency for the hollow needle to core the rubber sealing member as the needle is projected therethrough. The minute section or sliver cored from the rubber sealing member can plug the cannula to interfere with the flow of liquid or fluid through the needle and/or, if small enough, it can become entrained in the fluid or liquid as it is being dispensed from the device into the patient. The entrained rubber particle represents a foreign body. If the solution enters a blood stream, the potential danger is increased.

It is an object of this invention to provide a device of the type described wherein communication between the hollow needle and the fluid or liquid that is in the barrel can be effected without requiring the needle to pierce the sealing disc, thereby to avoid the danger heretofore described.

It is another object of this invention to provide a device of the type described, such as a syringe, vial, or infusion bottle in which use is made of a disc member.

It is another object of this invention to provide a device of the type described, such as a syringe, vial or infusion bottle, in which use is made of a disc member sealing the barrel but which instead is fabricated with sealing means displaceable within the barrel itself between a sealing position, separating the liquid within the barrel from the needle, and an unsealed position which enables the liquid to flow from the barrel into communication with the needle to enable liquid to be dispensed from the barrel and through the needle.

DESCRIPTION OF THE DRAWINGS

These and object objects of this invention will hereinafter appear and, for purposes of illustration, but not of limitation, embodiments of the invention are shown in the accompanying drawings, in which

FIG. 4 is an elevational view of the device of FIG. 3 showing the sealing means in unsealed position;

FIG. 5 is an elevational view showing a further ramification of this invention with the sealing means in sealing position;

FIG. 6 is an elevational view of the device in FIG. 5 showing the sealing means in unsealed position; and FIG. 7 is a bottom view of the sealing means of FIGS. 5 and 6.

BRIEF DESCRIPTION OF THE INVENTION

Figures 1, 2, 3:
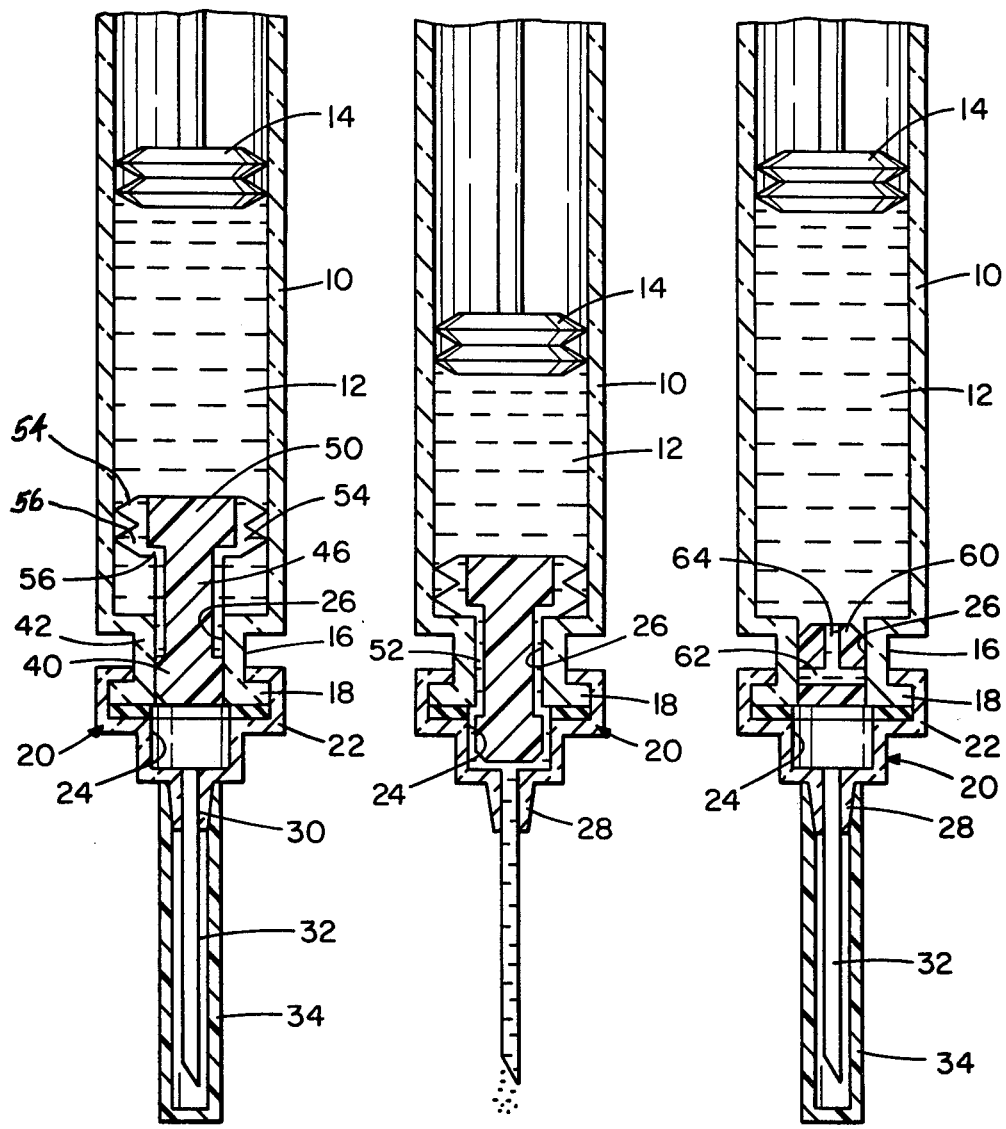
FIG. 1 is a sectional elevational view of a portion of the device mounting the hollow needle in position of use and of the sealing means embodying the features of this invention, with the sealing means in sealing position.
FIG. 2 is a sectional view of the portion of the device shown in FIG. 1 showing the sealing means in unsealed position.
FIG. 3 is an elevational view showing a modification in the device embodying the features of this invention, showing the sealing means in sealing position.

The invention is illustrated by reference to a syringe comprising an elongate barrel 10 of glass or plastic adapted to be filled with a liquid 12 to be dispensed from the barrel in response to displacement of a plunger 14 in sealing engagement with the upper end portion of the barrel. The barrel may be a single barrel for dispensing a liquid contained therein, as illustration in U.S. Pat. No. 3,401,693, or it may be the last of a series of telescoping barrels in which a liquid is displaced into the barrel 10 for admixture with another liquid or soluble particulate material, as illustrated in U.S. Pat. Nos. 3,682,194 and 3,757,779.

Instead of making use of a sealing disc required to be pierced by the needle to establish communication between the barrel and the needle for dispensing liquid from the barrel, the device embodying the features of this invention makes use of a sealing disc 40 dimensioned to have an outside diameter corresponding to the diameter of the elongate, cylindrical passage 26 through the neck of the barrel whereby the sealing disc 40 slidably engages the walls of the neck portion 16 in sealing relation to seal off the interior of the barrel from the open end of the barrel when the sealing disc is positioned within the neck portion 42 of the barrel.

Means are provided for establishing communication between the interior of the barrel 10 and the needle 32 for flow of liquid from the barrel to the needle in response to displacement of the sealing disc from within the neck portion of the barrel and for causing fluid to flow from the barrel to the needle in response to displacement of the plunger 14, as in the devices of the types previously described.

DETAILED DESCRIPTION OF THE INVENTION

In the illustrated modification the barrel 10 is formed with an open ended, elongated neck portion 16 of cylindrical shape which terminates in a lip 18 in the form of an annular flange. Secured onto the lip about the open end of the barrel is a hub member 20, one end portion of which is crimped, as at 22, about the lip for attachment thereto in sealing relation.

The hub member is offset inwardly beyond the lip portion to define a cylindrical chamber 24 having a cross section greater than the cross section of the cylindrical bore 26 through the neck end portion of the barrel and it terminates in a sleeve section 28 of lesser diameter having s passage 30 extending therethrough for supporting a hollow needle 32 with the inner end in communication with the chamber 24.

During periods of non-use, the needle 32 is enclosed by a needle cap 34 in the form of an elongate cylindrical member, the upper open end of which is dimensioned to correspond with the outer diameter of the sleeve section 28 for removably securing the needle cap 34 onto the hub member.

In the modification illustrated in FIGS. 1 and 2, the sealing disc is in the form of a cylindrical member 40 dimensioned to have a thickness less than the height of the chamber 24 of the hub member 20, and a diameter corresponding to the diameter of the cylindrical bore 26 slidably to engage the inner walls of the bore in sealing relation. At least the outer peripheral surface of the cylindrical member 40, and preferably the entire cylindrical member, is formed of rubber or rubber-like material whereby a sealing relation is maintained between the sealing disc and the cylindrical neck portion of the barrel while the sealing disc is located therein.

In operation, the vial is filled with the liquid content material 12 to be dispensed while the sealing disc 40 is within the bore whereby the liquid is retained within the barrel separated in sealing relation by the sealing disc from the needle 32. When the desired amount of liquid is introduced into the barrel, the plunger 14, inserted into the open upper end of the barrel, entraps the liquid in sealing relation within the barrel to enable storage, transportation or use in the assembled relation.

When it is desired to dispense liquid from the barrel, the needle cap 34 is removed, the sharp outer end of the hollow needle is inserted in the vein, vessel or the like, and the plunger is then displaced downwardly in the barrel, manually or by other means.

In response to axial displacement of the plunger 14, the liquid is displaced under pressure in the direction towards the open end of the barrel with corresponding axial displacement of the sealing disc 40. The sealing relation is maintained until the sealing disc clears the cylindrical passage 42 and enters into the chamber 24 of the hub member, as illustrated in FIG. 2, whereupon the liquid 12 is free to flow for passage under pressure into the chamber 24 and the hollow needle, as the plunger continues to be displaced into the barrel. Thus liquid is free to flow from the barrel and is forced by the plunger in pressurized flow from the barrel through the hollow needle and into the element into which the pointed end of the hollow needle has previously been inserted.

In the preferred modification, illustrated in FIGS. 1 and 2, means are provided to restrain the sealing disc 40 from obstructing the entrance to the hollow needle 32 when the sealing disc is displaced from sealing position within the passage 26 to unsealing position within the chamber 24. For this purpose the sealing disc 40 is connected by stem 46 to a stop member 50 on the upper end of the stem 46. The stop member is dimensioned to have a diameter greater than the diameter of the bore 42 and is spaced from the sealing disc 40 by an amount greater than the length of the bore 42 but less than the length of the bore plus the length of the chamber 24 minus the thickness of the sealing disc so that the base of the stop 50 will come into engagement with the portion of the barrel surrounding the inlet to the bore after the sealing disc 40 clears the open end of the bore but before it can come into engagement with the base of the chamber 24 where it might otherwise block the needle passage.

The stem 46 may be dimensioned to have a cross section less than the cross section of the passage 26 but it is preferred to form the stem with a cross section to correspond with the cross section of the bore but then vertically extending grooves 52 are provided in the peripheral portion to enable the flow of fluid or liquid therethrough from the barrel to the sealing disc 40 for communicating the interior of the barrel with the chamber 24 when the sealing disc has been displaced beyond the open end of the barrel. In the preferred modification, illustrated in FIGS. 1 and 2, the stop member 50 is dimensioned to have a diameter corresponding to the inner diameter of the barrel 10 for sliding engagement therewith. One or more grooves 54 extend axially along the periphery of the stop member with radially connecting grooves 56 across the bottom wall to enable free flow of liquid through the grooves 54 and 56 to the grooves 52 when the sealing disc has been displaced to unsealing position.

In the modification shown in FIGS. 3 and 4, the sealing disc 60 is in the form of a cylindrical member formed with one or more crosswise extending passages 62 intermediate the length of the cylindrical member with one or more passages 64 extending upwardly in the axial direction from the crosswise passages 62 through the remainder of the sealing disc. As in the previous modification, the sealing disc 60 is dimensioned in at least the portion below the crosswise passages 62 to engage the walls of the bore in sealing relation thereby to separate the portion of the barrel containing the liquid 12 from the open end of the barrel.

Again, in response to axial displacement of the plunger 14, the force operating through the liquid column 12 causes the sealing disc 60 to be displaced axially towards the open end of the barrel. As the portion of the sealing disc below the crosswise passage or passages clears the open end of the barrel, the crosswise passages 62 come into communication with the chamber 24 whereby liquid in the barrel is now free to flow through the vertical passage or passages 64 into the crosswise passage or passages 62 for flow into the chamber 24 and to the hollow injection needle 32. When such communication has been established, liquid pressure on the sealing disc 60 is relieved whereby the portion remaining in the bore is effective to retain the sealing disc so that it will not fall into the chamber 24 with the liquid.

In the modification shown in FIGS. 5-7, the sealing disc 70 is dimensioned to have a cross section or diameter slidably to engage the walls of the cylindrical passage through the neck of the barrel in sealing engagement, but less than the cross section of the chamber 24, and a thickness that is less than the depth of the chamber. Thus the sealing disc 70 separates the interior of the barrel from the chamber 24 to prevent liquid flow from the barrel into the chamber when the sealing disc 70 is located in sealing position within the cylindrical neck portion of the barrel.

In response to axial displacement of the plunger 14 into the barrel, the sealing disc 70 is displaced by reaction with the liquid content material until the sealing disc is displaced from sealing engagement with the cylindrical neck portion of the barrel. Thus the way is open for the liquid 12 to flow from the barrel into the chamber 24 and through the needle 32 to the member into which the needle has been inserted.

Since the sealing disc 70 can fall gravitationally and/or in response to fluid flow to the bottom of the chamber 24, where it can block the opening to the hollow needle, the bottom wall 72 of the sealing disc is provided with one or more grooves or troughs 74 which extend radially from the center to the outer edge, thereby to provide channels through which the liquid or fluid may flow from the chamber to the central opening communicating with the hollow needle 32. Thus, even when the sealing disc 70 is pressed downwardly by the fluid or liquid into engagement with the bottom wall of the chamber 24, to cover the needle opening, passages are available for the flow of fluid or liquid through the grooves or troughs to the needle.

It will be apparent from the foregoing that I have provided a device of the type described wherein the hollow needle remains fixed in the assembled device while use is made of a sealing disc that is axially slidable in the cylindrical passage through the neck portion of the barrel between sealing position and unsealing position to maintain separation of the fluid in the barrel from the needle when in sealing position, and to permit flow of fluid from the barrel to the needle when in non-sealing position thereby to enable dispensing of the liquid or fluid from the barrel without the need to project the hollow needle through a sealing disc.

It will be understood that changes may be made in the details of construction, arrangement and operation, without departing from the spirit of the invention, especially as defined in the following claims.

I claim:

1. A device for dispensing a fluid maintained in sealed relation therein comprising an elongate barrel having an open end and a cylindrical bore of lesser cross section in the end portion of the barrel leading to the open end, a hollow needle, a hub member secured at one end about the open end of the barrel and at the other end for mounting one end of the hollow needle, and a portion intermediate said end defining a chamber having a cross section greater than the cross section of the bore and in direct communication therewith, a plunger dimensioned slidably to engage the interior of the barrel in sealing relation, a sealing disc within said bore dimensionsed to engage the walls of said bore in sealing relation and axially slidable in said bore between a sealing position to seal off the space between said sealing disc and plunger and unsealing position to permit flow of fluid from the barrel to said chamber and to the hollow needle in communication therewith, a stem extending centrally upwardly from the sealing disc and dimensioned to have a cross sectional area less than the cross sectional area of the bore to provide a space therebetween, an abutment on the end of the stem spaced from the sealing disc by an amount greater than the length of the bore, the width of said abutment being substantially equal to the inner dimension of said barrel, and means for displacement of the plunger within the barrel.

2. A device as claimed in claim 1 in which the sealing disc is dimensioned to have a thickness less than the height of the chamber to enable displacement from the bore into the chamber in unsealing position.

3. A device as claimed in claim 1 wherein the abutment is spaced from the sealing disc by an amount less than the length of the bore plus the height of the chamber less the thickness of the sealing disc, axial grooves extending throughout the length of the stem and radially extending grooves in the bottom wall of the stem communicating with the axial grooves to enable the passage of liquid therethrough.

4. A device as claimed in claim 3 in which the stem connecting the sealing disc with the abutment is dimensioned to correspond with the inner dimension of the bore for sliding engagement therewith, and channels extending axially along the stem for communication with the radial grooves in the bottom wall of the abutment.

5. A device as claimed in claim 1 in which the sealing disc includes one or more passages extending crosswise through an intermediate portion of the sealing disc, and another passage or passages extending downwardly from the upper surface of the sealing disc into communication with said crosswise extending passage or passages whereby communication is established for the flow of fluid from the interior of the barrel through said passages and into the chamber when the sealing disc is displaced from the bore by an amount to enable the crosswise passages to clear the open end of the barrel.

6. A device as claimed in claim 2 which includes a passage extending axially from the center of the bottom wall of the chamber into communication with the hollow needle and in which the sealing disc includes one or more grooves extending radially in the bottom face of the sealing disc from the outer edge to the center to provide passages for the flow of fluid from the chamber to the needle even when the sealing disc is at rest on the bottom wall of the chamber.

7. A device as claimed in claim 1 in which the stem is dimensioned to have a cross section corresponding to the cross section of the bore and which includes grooves in the peripheral surfaces of the stem to enable the passage of fluid or liquid therethrough.

* * * * *